United States Patent [19]

Ackrell

[11] 4,130,654
[45] Dec. 19, 1978

[54] NOVEL 4-(8X-6,11-DIHYDRODIBENZO-[b.e.]-THIEPIN-11-ONE-3-YL)-4-OXOBUTYRIC ACIDS, METHODS OF PREPARATION, COMPOSITIONS AND USES THEREOF

[75] Inventor: Jack Ackrell, Palo Alto, Calif.

[73] Assignee: Syntex (U.S.A.) Inc., Palo Alto, Calif.

[21] Appl. No.: 873,300

[22] Filed: Jan. 30, 1978

[51] Int. Cl.$^2$ ............... A61K 31/385; C07D 337/12
[52] U.S. Cl. ............................... 424/275; 260/327 B
[58] Field of Search ............... 260/327 M; 424/275

[56] References Cited

U.S. PATENT DOCUMENTS

| 3,989,839 | 11/1976 | Ackrell | 424/275 |
|---|---|---|---|
| 4,000,288 | 12/1976 | Ackrell | 424/267 |
| 4,000,308 | 12/1976 | Ackrell | 424/275 |
| 4,025,640 | 5/1977 | McFadden et al. | 424/275 |
| 4,051,148 | 9/1977 | Prince et al. | 260/327 B |
| 4,051,149 | 9/1977 | Ackrell | 260/327 B |
| 4,051,150 | 9/1977 | Kluge | 260/327 B |
| 4,052,412 | 10/1977 | Bastian | 260/332.2 A |
| 4,055,574 | 10/1977 | Ackrell et al. | 260/327 B |
| 4,064,141 | 12/1977 | Ackrell | 260/327 B |

FOREIGN PATENT DOCUMENTS

| 2442979 | 3/1975 | Fed. Rep. of Germany | 260/327 B |
|---|---|---|---|
| 2606312 | 8/1976 | Fed. Rep. of Germany | 260/327 B |

OTHER PUBLICATIONS

Rajsner et al., Chem. Abstracts, vol. 79, abst. 78586w (1973).

Primary Examiner—John D. Randolph
Attorney, Agent, or Firm—Gerard A. Blaufarb

[57] ABSTRACT

This invention relates to novel 4-(8X-6,11-dihydrodibenzo-[b.e.]-thiepin-11-one-3-yl)-4-oxobutyric acids and their derivatives, wherein X is hydrogen, methoxy or chloro, methods of preparation, compositions and uses thereof.

19 Claims, No Drawings

NOVEL 4-(8X-6,11-DIHYDRODIBENZO-[B.E.]-THIEPIN-11-ONE-3-YL)-4-OXOBUTYRIC ACIDS, METHODS OF PREPARATION, COMPOSITIONS AND USES THEREOF

DESCRIPTION OF THE INVENTION

This invention relates to novel 4-(8X-6,11-dihydrodibenzo-[b.e.]-thiepin-11-one-3-yl)-4-oxobutyric acids and their derivatives of the formula:

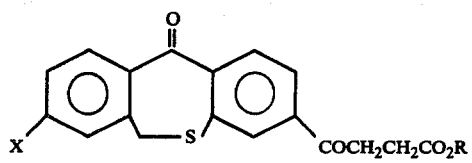

(A)

wherein X is hydrogen, methoxy or chloro, R is hydrogen, an alkyl group containing from one to twelve carbon atoms, or a pharmaceutically acceptable salt thereof when R is hydrogen, and methods for the preparation thereof.

Also included in this invention are compositions and methods of use for the compounds of Formula (A).

The term "alkyl" refers to and includes branched and straight chain hydrocarbons containing from one to twelve carbon atoms. Typical alkyl groups include methyl, ethyl, propyl, isopropyl, butyl, tertiary butyl, isoamyl, neopentyl, isopentyl, hexyl, octyl, nonyl, isodecyl, 6-methyldecyl, dodecyl, and the like.

The term "pharmaceutically acceptable salts" refers to salts prepared from pharmaceutically acceptable non-toxic bases including inorganic bases and organic bases. Salts derived from inorganic bases include sodium, potassium, lithium, ammonium, calcium, magnesium, ferrous, zinc, copper, manganous, aluminum, ferric manganic salts and the like. Particularly preferred are the ammonium, potassium, sodium, calcium and magnesium salts. Salts derived from pharmaceutically acceptable organic non-toxic bases include salts of primary, secondary, and tertiary amines, substituted amines including naturally occurring amines, cyclic amines and basic ion exchange resins, such as isopropylamine, trimethylamine, diethylamine, triethylamine, tripropylamine, ethanolamine, 2-dimethylaminoethanol, tromethamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, piperidine, tromethamine, choline and caffeine.

U.S. Pat. No. 4,052,412 discloses compounds having an oxobutyric moiety attached to a benzocycloheptathiophene nucleus and U.S. Pat. Nos. 4,000,288 and 4,000,308 disclose acetic and propionic acid moieties attached to a 6,11-dihydrodibenzo-thiepin-11-one nucleus.

The novel compounds of this invention are prepared according to the reaction scheme outlined in the flow sheet which follows:

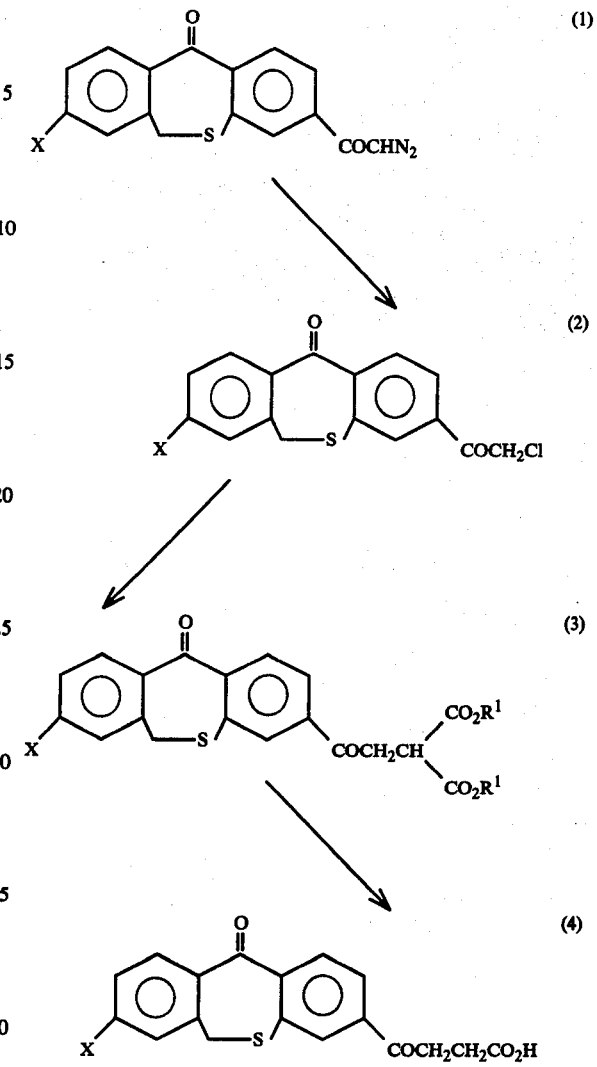

wherein X is hydrogen, methoxy or chloro and $R^1$ is the same alkyl group containing from 1 to 4 carbons, e.g., methyl, ethyl, propyl, isopropyl, butyl, and the like.

The compounds of Formula (1), obtained according to the preparations described more fully below, 3-diazoacetyl-6,11-dihydrodibenzo-[b.e.]-thiepin-11-one, 3-diazoacetyl-8-methoxy-6,11-dihydrodibenzo-[b.e.]-thiepin-11-one, and 3-diazoacetyl-8-chloro-6,11-dihydrodibenzo-[b.e.]-thiepin-11-one, are treated with hydrogen chloride gas at a temperature of from about −20° C. to about 25° C., preferably at about 0° C. to about 5° C., for from about 5 minutes to about 1 hour, preferably about 2 to about 10 minutes, in the presence of an inert organic solvent, e.g., methylene chloride, chloroform, tetrachloroethane, dimethoxyethane, and the like, or mixtures thereof, preferably methylene chloride, to obtain the compounds of Formula (2), 3-chloroacetyl-6,11-dihydrodibenzo-[b.e.]-thiepin-11-one, 3-chloroacetyl-8-methoxy-6,11-dihydrodibenzo-[b.e.]-thiepin-11-one, and 3-chloroacetyl-8-chloro-6,11-dihydrodibenzo-[b.e.]-thiepin-11-one, respectively.

The compounds of Formula (2) are treated with a dialkylmalonate, in which the alkyl goups are the same and contain from 1 to 4 carbon atoms, e.g., methyl, ethyl, propyl, isopropyl, butyl, and the like, at a temperature of from about 10° C. to about 50° C., preferably from about 20° C. to about 25° C., for from about 12 hours to about 72 hours, preferably from about 24 hours to about 48 hours, in the presence of an inert organic solvent, e.g., dimethylformamide, dimethylacetamide, N-methylpyrrolidone, and the like, or mixtures thereof, preferably dimethylformamide, in the presence of a base, e.g. potassium carbonate, sodium carbonate, lithium carbonate, and the like, to obtain the compounds of Formula (3), alkyl 2-carboalkoxy-4-(6,11-dihydrodibenzo-[b.e.]-thiepin-11-one-3-yl)-4-oxobutyrate,
alkyl 2-carboalkoxy-4-(8-methoxy-6,11-dihydrodibenzo-[b.e.]-thiepin-11-one-3-yl)-4-oxobutyrate, and
alkyl 2-carboalkoxy-4-(8-chloro-6,11-dihydrodibenzo-[b.e.]-thiepin-11-one-3-yl)-4-oxobutyrate, respectively wherein the alkyl and alkoxy groups contain from 1 to 4 carbon atoms.

The compounds of Formula (3) are then treated with an acid, an organic acid, e.g., acetic acid, propionic acid, and the like, an inorganic acid, e.g., phosphoric acid, hydrochloric acid, and the like, or mixtures thereof, e.g., a mixture of acetic acid and phosphoric acid, at a temperature of from about 50° C. to reflux, preferably at reflux, for from about one hour to about 8 hours, to obtain the compounds of Formula (4), 4-(6,11-dihydrodibenzo-[b.e.]-thiepin-11-one-3-yl)-4-oxobutyric acid,
4-(8-methoxy-6,11-dihydrodibenzo-[b.e.]-thiepin-11-one-3-yl)-4-oxobutyric acid, and
4-(8-chloro-6,11-dihydrodibenzo-[b.e.]-thiepin-11-one-3-yl)-4-oxobutyric acid, respectively.

It is to be understood that isolation of the compounds described herein, whether in the body of the specification, Examples or Preparations, can be effected, if desired, by any suitable separation or purification procedure, such as, for example, filtration, extraction, crystallization, column chromatography, thin-layer chromatography or thick-layer chromatography, or a combination of these procedures. Specific illustrations of suitable separation and isolation procedures can be had by reference to the Examples and Preparations hereinbelow. However, other equivalent separation or isolation procedures could, of course, also be used.

The salt derivatives of the compounds of Formula (4) are prepared by treating these free acids with an appropriate amount of a pharmaceutically acceptable base. Representative pharmaceutically acceptable bases are sodium hydroxide, potassium hydroxide, lithium hydroxide, ammonium hydroxide, calcium hydroxide, magnesium hydroxide, ferrous hydroxide, zinc hydroxide, copper hydroxide, manganous hydroxide, aluminum hydroxide, ferric hydroxide, manganic hydroxide, isopropylamine, trimethylamine, diethylamine, triethylamine, tripropylamine, ethanolamine, 2-dimethylaminoethanol, 2-diethylaminoethanol, tromethamine, lysine, arginine, histidine, caffeine, procaine, hydrabamine, choline, betaine, ethylenediamine, glucosamine, methylglucamine, theobromine, purines, piperazine, piperadine, N-ethylpiperidine, polyamine resins and the like. The reactions is conducted in water, alone or in combination with an inert, water-miscible organic solvent, at a temperature of from about 0° C. to about 100° C., preferably at room temperature. Typical inert, water-miscible organic solvents include methanol, ethanol, isopropanol, butanol, acetone, dioxane or tetrahydrofuran. The molar ratio of compounds of Formula (4) to base used are chosen to provide the ratio desired for any particular salt. For preparing, for example, the calcium salts or magnesium salts of the compounds of Formula (A) the free acid starting material of Formula (4) can be treated with at least one-half molar equivalent of pharmaceutically acceptable base to yield a neutral salt. When the aluminum salts of the compounds of Formula (A) are prepared, at least one-third molar equivalent of the pharmaceutically acceptable base are employed if a neutral salt product is desired.

In the preferred procedure, the calcium salts and magnesium salts of the compounds of Formula (A) can be prepared by treating the corresponding sodium or potassium salts of the compound of Formula (A) with at least one-half molar equivalent of calcium chloride or magnesium chloride, respectively, in an aqueous solution, alone or in combination with an inert water-miscible organic solvent, at a temperature of from about 20° C. to about 100° C. Preferably, the aluminum salt of the compounds of Formula (A) can be prepared by treating the corresponding free acids of the compounds of Formula (4) with at least one-third molar equivalent of an aluminum alkoxide, such as aluminum triethoxide, aluminum tripropoxide and the like, in a hydrocarbon solvent, such as benzene, xylene, cyclohexane, and the like at a temperature of from about 20° C. to about 115° C. Similar procedures can be used to prepare salts of inorganic bases which are not sufficiently soluble for easy reaction.

The salt products are isolated by conventional means. For example, the reaction mixtures are evaporated to dryness, and the salts can be further purified by conventional methods.

The salt derivatives of the compounds of Formula (4) can be reconverted to their respective free acids by acidifying said salts with an acid, preferably an inorganic acid, e.g., hydrochloric acid, sulfuric acid, and the like, at temperature of from about 0° C. to about 30° C., preferably at room temperature.

The esters of Formula (A) are prepared by esterifying the corresponding free acids of Formulas (4) with an alcohol reagent corresponding to the desired ester, e.g., an alkanol having up to 12 carbon atoms. This reaction is conducted in the presence of a strong acid, such as boron trifluoride, hydrogen chloride, sulfuric acid, p-toluenesulfonic acid, and the like. If the alcohol reagent used in the esterification is a liquid at the reaction temperature, the alcohol reagent can be the reaction solvent. Optionally, the reaction can be carried out in an inert organic solvent in which the free acids of Formula (4) and the alcohol reagent are soluble, such as a hydrocarbon solvent, e.g., hexane, isooctane, decane, cyclohexane, benzene, toluene, xylene, a halogenated hydrocarbon solvent, e.g., methylene chloride, chloroform, dichloroethane; or an ether solvent, e.g., diethyl ether, dibutyl ether, dioxane, tetrahydrofuran, and the like. In the case where the alcohol reagent is a solid, the reaction preferably is conducted in a non-aqueous liquid inert organic solvent. The reaction is conducted at from about 0° C. to the reflux temperature of the reaction mixture, preferably using hydrogen chloride at a temperature of from 15° C. to about 35° C.

The product is isolated by conventional means such as diluting the reaction mixture with water, extracting the resulting aqueous mixture with a water-immiscible inert organic solvent, such as diethyl ether, benzene, methylene chloride, and the like, combining the extracts, washing the extracts with water to neutrality and then evaporating under reduced pressure.

The preferred acid esters of Formula (A) are those ester derivatives prepared from methyl alcohol, ethyl alcohol, propyl alcohol, isopropyl alcohol, butyl alcohol, 2-butyl alcohol, isoamyl alcohol, pentyl alcohol, 2-pentyl alcohol, isopentyl alcohol, hexyl alcohol, 2-hexyl alcohol, isohexyl alcohol, heptyl alcohol, 2-heptyl alcohol, isoheptyl alcohol, octyl alcohol, 2-octyl alcohol, isooctyl alcohol, nonyl alcohol, 2-nonyl alcohol, isononyl alcohol, decyl alcohol, 2-decyl alcohol, isodecyl alcohol, undecyl alcohol, dodecyl alcohol, and the like.

Alternatively, the esters of Formula (A) can be prepared by transesterification, according to methods known in the art. It is preferred in preparing the esters via transesterification to go from a lower ester to a higher ester, e.g. from the methyl ester, for example, to the isoamyl ester, for example. However, by using a substantial excess of a lower alcohol, a higher ester can be transesterified to a lower ester; thus, for example, by using a substantial excess of ethanol, the hexyl ester is converted by the transesterification to the ethyl ester.

The compounds of Formula (A) and the esters and pharmaceutically acceptable salts thereof, are useful as anti-inflammatory agents, platelet aggregation inhibitors, fibrinolytic agents, and as smooth muscle relaxants. The compounds of Formula (A) and the esters and pharmaceutically acceptable salts thereof, can be used both prophylactically and therapeutically.

The compounds of Formula (A) and the esters and pharmaceutically acceptable salts thereof, exhibit anti-inflammatory, analgesic, platelet aggregation inhibition, and anti-pyretic activities. Accordingly, the compositions containing these compounds are useful in the treatment and elimination of inflammation such as inflammatory conditions of the muscular skeletal system, skeletal joints and other tissues, for example, in the treatment of inflammatory conditions such as rheumatism, concussion, laceration, arthritis, bone fractures, post-traumatic conditions, and gout. In those cases in which the above conditions include pain and pyrexia coupled with inflammation, the instant compounds are useful for the relief of these conditions as well as the inflammation.

In tests measuring a compound's, anti-inflammatory effect utilizing carrageenin induced paw inflammation in the rat, after the method of Winter et al, Proceedings for Experimental Biology and Medicine, Vol. 111, pages 544–547 (1962), the compounds of the present invention were found to possess anti-inflammatory activity, and at the doses tested, no untoward effects were observed.

Administration of a compound of Formula (A) and the esters and pharmaceutically acceptable salts thereof, in an appropriate pharmaceutical composition can be via any of the accepted modes of administration of agents for the treatment of inflammation, pain, or pyrexia, or the prophylaxis thereof. Thus, administration can be for example, orally, parenterally, or topically, in the form of solid, semi-solid or liquid dosage forms, such as, for example, tablets, suppositories, pills, capsules, powders, liquids, suspensions, creams, lotions, ointments, or the like, preferably in unit dosage forms suitable for simple administration of precise dosages. The compositions will include a conventional pharmaceutical carrier or excipient and a compound of Formula (A) and the esters and pharmaceutically acceptable salts thereof, and, in addition, may include other medicinal agents, pharmaceutical agents, carriers, adjuvants, etc.

The preferred manner of administration, for the conditions detailed above, is oral using a convenient daily dosage regiment which can be adjusted according to the degree of affliction. Generally, a daily dose of from 0.05 mg. to ten mg. of a compound of Formula (A) and the esters and pharmaceutically acceptable salts thereof, per kilogram of body weight is used. Most conditions respond to treatment comprising a dosage level of the order of 0.25 mg. to three mg. per kilogram of body weight per day. For such oral administration, a pharmaceutically acceptable non-toxic composition is formed by the incorporation of any of the normally employed excipients, such as, for example, pharmaceutical grades of mannitol, lactose, starch, magnesium stearate, sodium saccharin, talcum, cellulose, glucose, sucrose, magnesium carbonate, and the like. Such compositions take the form of solutions, suspensions, tablets, pills, capsules, powders, sustained release formulations and the like.

A compound of Formula (A) and the esters and pharmaceutically acceptable salts thereof, may be formulated into a suppository using, for example, polyalkylene glycols, for example, polypropylene glycol, as the carrier. Liquid pharmaceutically administerable compositions can, for example, be prepared by dissolving, dispersing, etc. an active compound, as described above, and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain a minor amount of non-toxic auxiliary substances such as wetting or emulsifying agents, pH buffering agents and the like, such as for example, sodium acetate, sorbitan monolaureate, triethanolamine oleate, etc.

Actual methods of preparing such dosage forms are known, or will be apparent, to those skilled in this art; for example, see Remington's *Pharmaceutical Sciences*, Mack Publishing Company, Easton, Pennsylvania, 14th Edition, 1970. The composition to be administered will, in any event, contain a quantity of active compound in a pharmaceutically effective amount for relief of the particular condition being treated in accordance with the teachings of this invention.

The compounds of Formula (A) and the esters and pharmaceutically acceptable salts thereof, described above, are also uterine smooth muscle relaxants and thus are useful as agents for maintaining the pregnancy of pregnant mammals, for the benefit of the mother and/or the fetus, until termination of the pregnancy is considered, from a medical point of view, to be favorable, or more favorable, for the mother and/or the fetus. It should be understood, however, that in certain instances, for example where parturition has already begun (i.e., the mother is experiencing uterine contractions, especially near full term), that administration of the compounds herein described may not maintain the pregnant state for an indefinite period of time. Rather, in such instances, the pregnancy will, most probably, be slightly "prolonged," a factor which may be advantageous to either the mother and/or the fetus.

In particular, the compounds of Formula (A) and the esters and pharmaceutically acceptable salts thereof, are used as agents for delaying the onset of, or for postponing, parturition. As used in this application, the phrase "to delay the onset of parturition" is intended to cover that delay in parturition caused by the administration of the compounds of Formula (A) and the esters and pharmaceutically acceptable salts thereof, at any time before uterine muscle contractions have begun. Thus, it is intended that the aforementioned phrase cover abortion prevention early in pregnancy (i.e., before the fetus is "viable") as well as delaying premature parturition, a term which sometimes is used with reference to that premature labor experienced later in the pregnancy when the fetus is considered to be "viable." In either case, the agents are administered as prophylactic agents in that such administration tends to prevent the onset of parturition. This administration is particularly useful in the treatment of women having a history of spontaneous abortion, miscarriage or premature delivery (i.e., delivery prior to full term). Such administration is also useful where there are clinical indications that the pregnancy might be terminated prior to that time and is considered favorable to the mother and/or fetus.

With respect to animals, this treatment can also be utilized to synchronize the deliveries from a group of pregnant animals to happen at or about the same time, or to happen at or about a desired time and/or place, when the births can be handled with greater facility.

As used in this application, the phrase "postponing parturition" is intended to cover that delay in parturition caused by the administration of the compounds of Formula (A) and the esters and pharmaceutically acceptable salts thereof after uterine muxcle contractions have begun. The condition of the patient, including the time within the gestation period when the contractions have begun, the severity of the contractions and how long the contractions have taken place will affect the results achieved with the administration of the compounds of Formula (A) and the esters and pharmaceutically acceptable salts thereof. For example, the effect can be to reduce the intensity and/or the duration of the contractions (the actual act of parturition being "prolonged"), or to stop the contractions altogether. In either case, the effect will be to prolong the gestation period although, depending upon the condition of the patient as described above, the effect may either be slight or, under appropriate circumstances, somewhat greater. Such administration may be to prevent spontaneous abortion, to cause the delivery to be more easily accomplished and/or less painful to the mother, or to occur at a more appropriate time and/or place.

In all cases, administration of the compounds of Formula (A) and the esters and pharmaceutically acceptable salts thereof, for the purposes set forth herein, should be consistent with best and/or accepted medical (or veterinary) practices so as to maximize the benefits to the mother and the fetus. For example, administration should not be continued so long past full term that the fetus dies in utero.

In the practice of the methods of the present invention, a therapeutically effective amount of a compound of Formula (A) and the esters and pharmaceutically acceptable salts thereof, or a pharmaceutical composition containing a compound of Formula (A) and the esters and pharmaceutically acceptable salts thereof, is administered to the pregnant mammal via any of the usual and acceptable methods known in the art. The compound can be administered either singly or in combination with another compound or compounds, as defined above, or other pharmaceutical agents, carriers, adjuvants, etc. Such compound(s) or compositions can be administered orally, parenterally, either in the form of solid, semi-solid, or liquid dosage forms. Typically, administration is by a pharmaceutical composition containing the pharmaceutically active compound and one or more pharmaceutical carriers or adjuvants.

The administerable composition may take the form or oral tablets, vaginal or uterine tablets or suppositories, pills, capsules, liquid solutions, suspensions, or the like, preferably in unit dosage forms suitable for simple administration of precise dosages. Conventional non-toxic solid carriers include, for example, pharmaceutical grades of mannitol, lactose, starch, magnesium stearate, sodium saccharine, talcum, cellulose, glucose, sucrose, magnesium carbonate, and the like. The active compound as defined above may be formulated as suppositories using, for example, polyalkylene glycols, for example, polypropylene glycol, as the carrier. Liquid pharmaceutically administerable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of non-toxic auxiliary substances such as wetting or emulsifying agents, pH buffering agents and the like, for example, sodium acetate, sorbitan monolaurate, triethanolamine oleate, etc. Actual methods of preparing such dosage forms are known, or will be apparent, to those skilled in this art; for example, see Remington's *Pharmaceutical Sciences*, Mack Publishing Company, Easton, Pennsylvania, 14th Edition, 1970. The composition or formulation to be administered will, in any event, contain a quantity of the compound(s) in an amount effective to delay the onset of parturition or to postpone parturition if uterine contractions have already begun. Generally a daily dose of from five mg. to about 250 mg. of the active compound per kilogram of body weight will be administered, with administration being a single daily dose or up to three or four smaller doses regularly given throughout the day. The amount of compound administered will, of course, depend on its relative activity.

DESCRIPTION OF SPECIFIC EMBODIMENTS

The following specific description, recited in the Examples (and Preparations) below, is given to enable those skilled in this art to more clearly understand and practice the present invention. They should not be considered as a limitation upon the scope of the invention but merely as being illustrative and representative thereof.

Where necessary, examples are repeated to prepare additional material for later examples; and unless otherwise specified, the reactions are carried out at room temperature (20° C. to 30° C.).

Preparation 1

200 G. of nitroterephthalic acid is dissolved in one liter of isopropanol and the thus-obtained solution is saturated with hydrogen chloride and refluxed for 3 days. (During this period, hydrogen chloride is passed into the solution occasionally in order to maintain the concentration thereof.) The reaction solution is then cooled and the isopropanol is removed by evaporation under reduced pressure to give a residue which is dissolved in 500 ml. of methylene chloride. The resultant solution is washed with 10% aqueous sodium carbonate, and the organic layer obtained is dried over magnesium sulfate, followed by removal of the solvent in vacuo to give 245 g. (yield 97.5%) of diisopropyl nitroterephthalate (1), an oil; IR: $\gamma_{max.}^{CHCl_3}$ 1724, 1542, 1350 cm.$^{-1}$; NMR: $\delta_{TMS}^{CDCl_3}$ 1.35 (6H, d), 1.40 (6H, d), 5.24 (1H, 7 lines), 5.27 (1H, 7 lines), 7.71 (1H, d), 8.24 (1H, dd), 8.43 ppm (1H, d).

Preparation 2

(a) 5.1 G. of sodium hydride is slowly added to a cooled ($-20°$ C.) solution of 23.5 ml of benzyl mercaptan in 100 ml. of dimethylformamide. The resultant solution is cooled to $-30°$ C. and there is added thereto 53 g. of diisopropyl nitroterephthalate in 100 ml. of dimethylformamide. After one hour at $-30°$ C. and 2 hours at 0° C., the reaction mixture is poured into water, the precipitate is filtered off, washed with water and dried to yield 77-92% of crude diisopropyl(benzylthio)-terephthalate, a sample of which, following recrystallization from pentane, melts at 70°-71° C.

(b) 0.94 G. of sodium hydride (50% in oil) is slowly added to a cooled ($-20°$ C.) solution of m-methoxybenzyl mercaptan (3.0 g) in 5 ml. of dimethylformamide. The resultant solution is cooled to $-30°$ C. and there is added thereto 5.2 g. of diisopropyl nitroterephthalate in 10 ml. of dimethylformamide. After 30 minutes at $-30°$ C., and 2 hours at room temperature the reaction mixture is poured into water (100 ml.) and extracted with two 50 ml. portions of benzene. The benzene extracts are combined, washed, dried and evaporated to yield a residue which is purified by chromatography on alumina eluting with hexane:ethyl acetate (1:6), followed by evaporation of the eluate to yield 5.53 g. (yield 78%) of diisopropyl-(m-methoxybenzylthio)-terephthalate, which after recrystallization from methanol has a melting point of 52°-43° C.

(c) Following the procedure of Preparation 2(b), and substituting a stoichiometric equivalent amount of m-chlorobenzyl mercaptan for m-methoxybenzyl mercaptan there is obtained, in 73% yield, diisopropyl-(m-chlorobenzylthio)-terephthalate, which after recrystallization from methanol has a melting point of 63°-64° C.

Preparation 3

(a) The diisopropyl-(benzylthio)-terephthalate obtained in Preparation 2 is refluxed with 500 ml. of methanol, 25 g. of potassium hydroxide and 50 ml. of water for 2 hours. The reaction mixture is then concentrated to a small volume, cooled, diluted with water and filtered through diatomaceous earth (Celite). The thus-obtained filtrate is acidified with 4N hydrochloric acid and the precipitate with forms is collected by filtraton and dried in an oven at 90°-100° C. to yield 45 g. (yield 87%) of (benzylthio)-terephthalic acid having a melting point of 299°-300° C.

(b) Following the procedure of Preparation 3(a), but substituting 32 g. of diisopropyl-(m-methoxybenzylthio)-terephthalate for diisopropyl-(benzylthio)-terephthalate, using 350 ml. of methanol, 35 ml. of water and 18 g. of potassium hydroxide, and refluxing for three hours, there is obtained 25.2 g. (yield 100%) of (m-methoxybenzylthio)-terephthalic acid having a melting point of 255°-256° C. after recrystallization from methanol.

(c) Following the procedure of Example 3(b) but substituting 24.8 g diisopropyl-(m-chlorobenzylthio)-terephthalate for diisopropyl-(m-methoxybenzylthio)-terephthalate, and using 250 ml. of methanol, 50 ml. of water and 13.7 g. of potassium hydroxide there is obtained 19.5 g. (yield 100%) of (m-chlorobenzylthio)-terephthalic acid having a melting point of 279°-280° C. after recrystallization from methanol.

Preparation 4

(a) 10 G. of (benzylthio)-terephthalic acid is treated with 10 ml. of thionyl chloride and the reaction mixture is refluxed for four hours. After removal of the excess thionyl chloride in vacuo, the residue obtained is slurried with hexane and the solid product is filtered off to yield 10.2 g. (yield 92%) of (benzylthio)-terephthalyl chloride hving a melting point of 158° C.

(b) A solution of 5 g. of (m-methoxybenzylthio)-terephthalic acid in 20 ml. of dioxane and 5.5 ml. of thionyl chloride is refluxed for 4 hours. The reaction mixture is cooled to room temperature and evaporated to yield a residue which is slurried with cold ether and filtered to yield 5.25 g. (yield 94%) of (m-methoxybenzylthio)-terephthalyl chloride having a melting point of 88°-90° C.

(c) Following the procedure of Preparation 4(b) but substituting 19 g. (m-chlorobenzylthio)-terephthalic acid for (m-methoxybenzylthio)-terephthalic acid, using 80 ml. of dioxane and 16.9 ml. of thionyl chloride, there is obtained (m-chlorobenzylthio)-terephthalyl chloride having the following physical constants: IR: $\gamma_{max.}^{film}$ 1750, 1600 cm.$^{-1}$.

Preparation 5

(a) 10.2 G. of (benzylthio)-terephthalyl chloride in 100 ml. of methylene chloride is added to a solution of 14.75 g. of aluminum chloride in 100 ml. of methylene chloride containing 10.51 ml. of nitromethane. After five hours at 25° C., 16.5 ml. of saturated aqueous sodium chloride is added with vigorous stirring. The inorganic salts which precipitated are filtered off and the filtrate is evaporated to dryness to give a solid residue which is slurried with ether. The ether slurry is filtered to give 7.0 g. (yield 70.7%) of 6,11-dihydrodibenzo-[b.e.]-thiepin-11-one-3-carbonyl chloride having a melting point of 119°-120° C.

(b) Following the procedure of Preparation 5(a) but substituting metric 23 g of (m-methoxybenzylthio)-terephthalyl chloride in 50 ml. of methylene chloride for (benzylthio)-terephthalyl chloride, using 25.3 g. of aluminum chloride and 100 ml. of methylene chloride containing 13.8 ml. of nitromethane, and treating for 2 hours at 0° C. there is obtained 18 g. (yield 78.5%) of 8-methoxy-6,11-dihydrodibenzo-[b.e.]-thiepin-11-one-3-carbonyl chloride having a melting point of 117°-118° C.

(c) A solution of 19 g. of (m-chlorobenzylthio)-terephthalyl chloride in 150 ml. of methylene chloride is added to a solution of 20.9 g. of aluminum chloride in 100 ml. of methylene chloride containing 19 ml. of nitromethane. After 16 hours at room temperature, 20.9 ml. of saturated aqueous sodium chloride is added with vigorous stirring. The inorganic salts which precipitate are filtered off and the filtrate is refluxed with 100 ml. of methanol for 1 hour, followed by evaporation to leave a residue which is crystallized from methanol to yield 10.2 g. (yield 61%) of methyl 8-chloro-6,11-dihydrobenz-[b.e.]-thiepin-11-one-3-carboxylate having a melting point of 161°–162° C., which after base hydrolysis, according to the procedure set forth in Preparation 3(b), yielded 8-chloro-6,11-dihydrodibenz-[b.e.]-thiepin-11-one-3-carboxylic acid (yield 90%) having a melting point of 274°–275° C. after recrystallization from methanol.

A solution of 0.3 g. of 8-chloro-6,11-dihydrodibenz-[b.e.]-thiepin-11-one-3-carboxylic acid in 10 ml. of dioxane containing one ml. of thionyl chloride is refluxed for two hours. The reaction mixture is cooled and evaporated to dryness to yield a residue which is slurried with a little cold ether (5 ml.). The ether slurry is filtered to yield 0.3 g. (yield 94%) of 8-chloro-6,11-dihydrodibenzo-[b.e.]-thiepin-11-one-3-carbonyl chloride having a melting point of 102°–103° C.

Preparation 6

(a) A solution of 11 g. of 6,11-dihydrodibenzo-[b.e.]-thiepin-11-one-3-carbonyl chloride in 100 ml. of methylene chloride is slowly added to excess diazomethane (prepared from 20 g. N-nitroso N-methylurea) in 200 ml. of ether solution. After 2 hours the reaction mixture is concentrated to about 50 ml. by boiling off the solvent, followed by cooling. The cooled reaction mixture is filtered to give a residue of 9.5 g. (yield 85%) of 3-diazoacetyl-6,11-dihydrodibenzo-[b.e.]-thiepin-11-one having a melting point of 153° C., with decomposition.

(b) Following the procedure of Preparation 6(c) but substituting 11 g. of 8-methoxy-6,11-dihydrodibenzo-[b.e.]-thiepin-11-one-3-carbonyl chloride for 6,11-dihydrodibenzo-[b.e.]-thiepin-11-one-3-carbonyl chloride there is obtained 7.5 g. (yield 78%) of 3-diazoacetyl-8-methoxy-6,11-dihydrodibenzo-[b.e.]-thiepin-11-one having a melting point of 147°–148° C., with decomposition.

(c) Following the procedure of Preparation 6(a) but substituting 4 g. of 8-chloro-6,11-dihydrodibenzo-[b.e.]-thiepin-11-one-3-carbonyl chloride for 6,11-dihydrodibenzo-[b.e.]-thiepin-11-one-3carbonyl chloride there is obtained 3 g. (yield 75%) of 3-diazoacetyl-8-chloro-6,11-dihydrodibenzo-[b.e.]-thiepin-11-one having a melting point of 155° C., with decomposition.

EXAMPLE 1

A solution of 4.0 g. of 3-diazoacetyl-6,11-dihydrodibenzo-[b.e.]-thiepin-11-one (1a) in 100 ml. of methylene chloride is cooled to −20° C. A rapid stream of hydrogen chloride gas is bubbled through the solution for a 5 minute period, with stirring. The reaction mixture is then evaporated to dryness. The residue thus-obtained is recrystallized from ethyl acetate to yield 4.0 g. of 3-chloroacetyl-6,11-dihydrodibenzo-[b.e]-thiepin-11-one (2a), having a melting point of 165°–166° C.

Similarly substituting a stoichiometric equivalent amount of 3-diazoacetyl-8-methoxy-6,11-dihydrobenzo-[b.e.]-thiepin-11-one (1b) and 3-diazoacetyl-8-chloro-6,11-dihydrodibenzo[b.e.]-thiepin-11-one (1c) for 3-diazoacetyl-6,11-dihydrodibenzo-[b.e.]-thiepin-11-one, there are obtained 3-chloroacetyl-8-methoxy-6,11-dihydrodibenzo-[b.e.]-thiepin-11-one (2b), having a melting point of 170°–171° C., and 3-chloroacetyl-8-chloro-6,11-dihydrodibenzo-[b.e.]-thiepin-11-one (2c), respectively.

EXAMPLE 2

200 Mg. of 3-chloroacetyl-6,11-dihydrodibenzo-[b.e.]-thiepin-11-one (2a) is stirred for 24 hours at room temperature with 1.5 ml. of dimethyl malonate and 0.5 g. of potassium carbonate. The reaction mixture is filtered and the filtrate chromatographed on 20 g. of silica gel eluting with hexane:ethyl acetate (5:1) to yield 225 mg. of methyl 2-(carboxymethoxy-4-(6,11-dihydrodibenzo-[b.e.]-thiepin-11-one-3-yl)-4-oxobutyrate (3a), a pale yellow oil, having a UV: $\lambda_{max.}^{MeOH}$ 252, 281, 380 m$\mu$ ($\epsilon$ 24,100, 14,400, 2800); IR: $\gamma_{max.}^{CHCl_3}$ 1745, 1730, 1685, 1645, 1595 cm.$^{-1}$; NMR: $\delta_{TMS}^{CDCl_3}$ 3.60 (2H,d), 3.65 (1H,t), 3.76 (6H,s), 4.08 (2H,s), 7.22–7.98 (6H,m); 8.25 ppm (1H,d).

In like manner substituting a stoichiometric equivalent amount of 3-chloroacetyl-8-methoxy-6,11-dihydrodibenzo-[b.e.]-thiepin-11-one (2b), and 3-chloroacetyl-8-chloro-6,11-dihydrodibenzo-[b.e.]-thiepin-11-one (2c), for 3-chloroacetyl-8-6,11-dihydrodibenzo-[b.e.]-thiepin-11-one, conducting the reaction for 72 rather than 24 hours, and substituting diethyl malonate for dimethyl malonate there is obtained ethyl 2-carbethoxy-4-(8-methoxy-6,11-dihydrodibenzo-[b.e.]-thiepin-11-one-3-yl)-4-oxobutyrate (3b), in 92% yield, having a melting point of 73°–75° C., after recrystallization from methanol/water, and ethyl 2-carboethoxy-4-(8-chloro-6,11-dihydrodibenzo-[b.e.]-thiepin-11-one-3-yl)-4-oxobutyrate (3c), respectively.

Other dialkyl malonates can be used in place of dimethyl malonate or diethyl malonate to yield, for example, propyl 2-carbopropoxy-4-(6,11-dihydrodibenzo-[b.e.]-thiepin-11-one-3-yl)-4-oxobutyrate (3a), propyl 2-(carbopropoxy-4-(8-methoxy-6,11-dihydrodibenzo-[b.e.]-thiepin-11-one-3-yl)-4-oxobutyrate (3b), propyl 2-carbobutyroxy-4-(8-chloro-6,11-dihydrodibenzo-[b.e.]-thiepin-11-one-3-yl)-4-oxobutyrate (3c), and the like.

EXAMPLE 3

A solution of 400 mg. of methyl 2-carbomethoxy-4-(6,11-dihydrodibenzo-[b.e.]-thiepin-11-one-3-yl)-4-oxobutyrate (3a) in a mixture of 10 ml. of acetic acid and 10 ml. of phosphoric acid is refluxed for one hour. The reaction mixture is cooled to room temperature and poured into 100 g. of ice and extracted with two 50 ml. portions of ethyl acetate. The extracts are combined, washed with water and extracted with two 10 ml. portions of 10% aqueous sodium carbonate solution. The basic extracts are combined and acidified to pH one with dilute hydrochloric acid and extracted with two 25 ml. portions of ethyl acetate. The extracted organic layers are combined, washed, dried over magnesium sulfate and evaporated to yiueld a residue which is extracted with three 5 ml. portions of boilding ether. The ether extracts are combined, evaporated to a volume of about 5 ml., followed by cooling to 0° C. and maintained at that temperature for one hour to yield 248 mg. of pale yellow prisms of 4-(6,11-dihydrodibenzo-[b.e.]-thiepin-11-one-3-yl)-4-oxobutyric acid (4a) having a melting point of 150°-151° C.

In like manner substituting a stoichrometric equivalent amount of ethyl 2-carboethoxy-4-(8-methoxy-6,11-dihydrodibenzo-[b.e.]-thiepin-11-one-3-yl)-4-oxobutyrate (3b) for methyl 2-carbomethoxy-4-(6,11-dihydrodibenzo-[b.e.]-thiepin-11-one-3-yl)-4-oxobutyrate (3a) and refluxing for 3 hours rather than one hour there is obtained 4-(8-methoxy-6,11-dihydrodibenzo-[b.e.]-thiepin-11-one-3-yl)-4-oxobutyric acid (4b) having a melting point of 163°-165° C.

Similarly, by following the procedure outlined immediately above ethyl 2-carboethoxy-4-(8-chloro-6,11-dihydrodibenzo-[b.e.]-thiepin-11-one-3-yl)-4-oxobutyrate (3c) is converted to 4-(8-chloro-6,11-dihydrodibenzo-[b.e.]-thiepin-11-one-3-yl)-4-oxobutyric acid (4c).

Likewise, other alkyl 2-carboalkoxy-4-(8-unsubstituted- and 8-methoxy- and 8-chloro-6,11-dihydrodibenzo-[b.e.]-thiepin-11-one-3-yl)-4-oxobutyrates (3), for example, propyl 2-carbopropoxy-4-(6,11-dihydrodibenzo-[b.e.]-thiepin-11-one-3-yl)-4-oxobutyrate (3a),
propyl 2-carbopropoxy-4-(8-methoxy-[b.e.]-thiepin-11-one-3-yl)-4-oxobutyrate (3b), and
butyryl 2-carbobutyroxy-4-(6-chloro-[b.e.]-thiepin-11-one-3-yl)-4-oxobutyrate (3c), are converted to their corresponding 4-(8-unsubstituted- and 8-methyl- and 8-chloro-6,11-dihydrodibenzo-[b.e.]-thiepin-11-one-3-yl)-4-butyric acids (4), for example,
4-(6,11-dihydrodibenzo-[b.e.]-thiepin-11-one-3-yl)-4-oxobutyric acid (4a),
4-(8-methoxy-6,11-dihydrodibenzo-[b.e.]-thiepin-11-one-3-yl)-4-oxobutyric acid (4b), and
4-(8-chloro-6,11-dihydrodibenzo-[b.e.]-thiepin-11-one-3-yl)-4-oxobutyric acid (4c).

EXAMPLE 4

100 Mg. of 4-(6,11-dihydrodibenzo-[b.e.]-thiepin-11-one-3-yl)-4-oxobutyric acid is dissolved in five ml. of methanol and the solution is saturated with hydrogen chloride. After 24 hours, the excess alcohol is distilled off in vacuo and the residue is purified by chromatography on alumina to yield methyl 4-(6,11-dihydrodibenzo-[b.e.]-thiepin-11-one-3-yl)-4-oxobutyrate.

Likewise other esters, e.g., ethyl, propyl, isopropyl, isoamyl, hexyl, nonyl, dodecyl, and the like of 4-(6,11-dihydrodibenzo-[b.e.]-thiepin-11-one-3-yl)-4-oxobutyric acid are obtained by substituting other alcohols, e.g., ethyl, propyl, isopropyl, isoamyl, hexyl, nonyl, dodecyl, alcohol, and the like, for methanol.

Similarly, by substituting the 4-(8-methoxy- and 8-chloro-6,11-dihydrodibenzo-[b.e.]-thiepin-11-one-3-yl)-4-oxobutyric acids, with the appropriate alcohol there are obtaned the methyl, ethyl, propyl, isopropyl, isoamyl, hexyl, nonyl, dodecyl, and the like, esters of 4-(8-methoxy- and 8-chloro-(6,11-dihydrodibenzo-[b.e.]-thiepin-11-one-3-yl)-4-oxobutyric acid.

EXAMPLE 5

100 Mg. of 4-(6,11-dihydrodibenzo-[b.e.]-thiepin-11-one-3-yl)-4-oxobutyric acid in five ml. of methanol is treated with methanolic potassium hydroxide containing one equivalent of potassium hydroxide. The solvent is evaporated in vacuo and the residue taken up in 2 ml. of methanol, followed by precipitation with ether to yield potassium 4-(6,11-dihydrodibenzo-[b.e.]-thiepin-11-one-3-yl)-4-oxobutyrate.

Likewise other salts, e.g., ammonium and sodium, of 4-(6,11-dihydrodibenzo-[b.e.]-thiepin-11-one-3-yl)-4-oxobutyric acid are prepared by substituting ammonium hydroxide and sodium hydroxide for potassium hydroxide in the procedure described above.

EXAMPLE 6

100 Mg. of 4-(8-methoxy-6,11-dihydrodibenzo-[b.e.]-thiepin-11-one-3-yl)-4-oxobutyric acid in one ml. of methanol is treated with methanolic potassium hydroxide containing one equivalent of potassium hydroxide. The solvent is stripped and 5 ml. of toluene is added. The thus obtained toluene solution is evaporated to dryness to give potassium 4-(8-methoxy-6,11-dihydrodibenzo-[b.e.]-thiepin-11-one-3-yl)-4-oxobutyrate.

Likewise other salts, e.g., ammonium and sodium of 4-(8-methoxy-6,11-dihydrodibenzo-[b.e.]-thiepin-11-one-3-yl)-4-oxobutyric acid are prepared by substituting, e.g., ammonium hydroxide and sodium hydroxide for potassium hydroxide in the procedure described above.

Similarly, by substituting 4-(8-chloro-6,11-dihydrodibenzo-[b.e.]-thiepin-11-one-3-yl)-4-oxobutyric with the appropriate hydroxide, there is obtained the potassium, ammonium, and sodium salts of 4-(8-chloro-6,11-dihydrodibenzo-[b.e.]-thiepin-11-one-3-yl)-4-oxobutyric acid.

EXAMPLE 7

200 Mg. of 4-(6,11-dihydrodibenzo-[b.e.]-thiepin-11-one-3-yl)-4-oxobutyric acid is dissolved in an excess of 1N aqueous sodium hydroxide and the resultant solution is buffered with 0.3 g. of ammonium chloride. The buffered solution is added to a solution of 200 mg. of calcium carbonate in 1N aqueous hydrochloric acid. The precipitate which forms is collected by filtration, washed consecutively with water, dimethoxyethane and ether, to yield calcium 4-(6,11-dihydrodibenzo-[b.e.]-thiepin-11-one-3-yl)-4-oxobutyrate.

Likewise magnesium 4-(6,11-dihydrodibenzo-[b.e.]-thiepin-11-one-3-yl)-4-oxobutyrate is prepared by substituting magnesium carbonate for calcium carbonate.

EXAMPLE 8

50 Mg. of 4-(8-methoxy-6,11-dihydrodibenzo-[b.e.]-thiepin-11-one-3-yl)-4-oxobutyric acid in 5 ml. of methanol is treated with 1N methanolic potassium hydroxide to a faint orange color, followed by discharging the color by the addition of 1 mg. of 4-(8-methoxy-6,11-dihydrodibenzo-[b.e.]-thiepin-11-one-3-yl)-4-oxobutyric acid, yielding a solution containing potassium 4-(8-methoxy-6,11-dihydrodibenzo-[b.e.]-thiepin-11-one-3-yl)-4-oxobutyrate. A solution of 40 mg. of calcium carbonate dissolved in the minimum amount of 1 N hydrochloric acid necessary to effect solution of the calcium carbonate, is buffered with 100 mg. of solid ammonium chloride, followed by the further addition of five ml. of water. The thus obtained buffered calcium solution is then added to the solution of potassium 4-(8-methoxy-6,11-dihydrodibenzo-[b.e.]-thiepin-11-one-3-yl)-4-oxobutyrate to yield a precipitate. The precipitate is collected, washed with water and dried at room temperature to yield calcium 4-(8-methoxy-6,11-dihydrodibenzo-[b.e.]-thiepin-11-one-3-yl)-4-oxobutyrate.

Likewise magnesium 4-(8-methoxy-6,11-dihydrodibenzo-[b.e.]-thiepin-11-one-3-yl)-4-oxobutyrate is prepared by substituting magnesium carbonate for calcium carbonate.

Similarly, by substituting 4-(8-chloro-(6,11-dihydrodibenzo-[b.e.]-thiepin-11-one-3-yl)-4-oxobutyric with the appropriate carbonate there is obtained the calcium and magensium salts of 4-(8-chloro-6,11-dihydrodibenzo-[b.e.]-thiepin-11-one-3-yl)-4-oxobutyric acid.

EXAMPLE 9

200 Mg. of 4-(6,11-dihydrodibenzo-[b.e.]-thiepin-11-one-3-yl) 4-oxobutyric acid in one ml. of methanol is treated with 1N methanolic potassium hydroxide to a faint orange color. A small amount of solid 4-(6,11-dihydrodibenzo-[b.e.]-thiepin-11-one-3-yl)-oxobutyric acid is added to decolorize the solution. The solvent is stripped and the residue is dissolved in five ml. of water. The thus obtained aqueous solution of potassium 4-(6,11-dihydrodibenzo-[b.e.]-thiepin-11-one-3-yl)-4-oxobutyrate is added to a solution of 150 mg. of cupric nitrate trihydrate in five ml. of water. The precipitate which forms is collected, washed with water and dried in air to yield copper 4-(6,11-dihydrodibenzo-[b.e.]-thiepin-11-one-3-yl)-4-oxobutyrate.

EXAMPLE 10

200 Mg. of 4-(8-methoxy-6,11-dihydrodibenzo-[b.e.]-thiepin-11-one-3-yl)-4-oxobutyric acid in one ml. of methanol is titrated with 1N methanolic potassium hydroxide to a faint orange color. A small amount of 4-(8-methoxy-6,11-dihydrodibenzo-[b.e.]-thiepin-11-one-3-yl)-4-oxobutyric acid is added to decolorize the solution. The solvent is stripped and the residue is dissolved in five ml. of water. The thus obtained aqueous solution of potassium 4-(8-methoxy-6,11-dihydrodibenzo-[b.e.]-thiepin-11-one-3-yl)-4-oxobutyrate is added to a solution of 150 mg. of cupric nitrate trihydrate in five ml. of water. The precipitate which forms is collected, washed with water and dried in air to yield copper 4-(8-methoxy-6,11-dihydrodibenzo-[b.e.]-thiepin-11-one-3-yl)-4-oxobutyrate.

Similarly, substituting 4-(8-chloro-6,11-dihydrodibenzo-[b.e.]-thiepin-11-one-3-yl)-4-oxobutyric acid is productive of the copper salt of 4-(8-chloro-6,11-dihydrodibenzo-[b.e.]-thiepin-11-one-3-yl)-4-oxobutyric acid.

EXAMPLE 11

100 Mg. of 4-(6,11-dihydrodibenzo-[b.e.]-thiepin-11-one-3-yl)-4-oxobutyric acid in 15 ml. of hot benzene is treated with 60 mg. of isopropyl amine. The solution is allowed to cool to room temperature and the product is filtered off, washed with ether and dried to yield isopropylammonium 4-(6,11-dihydrodibenzo-[b.e.]-thiepin-11-one-3-yl)-4-oxobutyrate.

Likewise other salts, e.g. amine salts, such as diethylamine, ethanolamine, piperidine, tromethamaine, choline, and caffeine, of 4-(6,11-dihydrodibenzo-[b.e.]-thiepin-11-one-3-yl)-4-oxobutyric acid are prepared by substituting each of the respective amines for isopropylamine.

EXAMPLE 12

100 Mg. of 4-(8-methoxy-6,11-dihydrodibenzo-[b.e.]-thiepin-11-one-3-yl)-4-oxobutyric acid in 10 ml. of benzene is treated with 60 mg. of piperidine. The solution obtained is allowed to stand for one hour and the crystalline material which forms is filtered, washed with ether and air dried to yield piperidinium 4-(8-methoxy-6,11-dihydrodibenzo-[b.e.]-thiepin-11-one-3-yl)-4-oxobutyrate.

Likewise other salts, e.g., amine salts, e.g., isopropylamine, diethylamine, ethanolamine, tromethamine, choline, and caffeine, of 4-(8-methoxy-6,11-dihydrodibenzo-[b.e.]-thiepin-11-one-3-yl)-4-oxobutyrate are prepared by substituting each of the respective amines for piperidine.

Similarly, substituting 4-(8-chloro-6,11-dihydrodibenzo-[b.e.]-thiepin-11-one-3-yl)-4-oxobutyric acid is productive of the amine salts, e.g., piperidine, isopropylamine, diethylamine, ethanolamine, tromethamine, choline and caffeine, of 4-(8-chloro-6,11-dihydrodibenzo-[b.e.]-thiepin-11-one-3-yl)-4-oxobutyric acid.

EXAMPLE 13

One gram of potassium 4-(6,11-dihydrodibenzo-[b.e.]-thiepin-11-one-3-yl)-4-oxobutyrate is dissolved in 50 ml. of water and the solution is acidified with 20 ml. of 3N aqueous hydrochloric acid. The reaction mixture is extracted twice with ethyl acetate (25 ml. portions) and the extracts are combined, washed with 50 ml. of water and dried over magnesium sulfate. The solvent is evaporated under reduced pressure and the residue is recrystallized from benzene to yield 4-(6,11-dihydrodibenzo-[b.e.]-thiepin-11-one-3-yl)-4-oxobutyric acid.

Similarly, other salts, e.g., sodium, ammonium, calcium, amine, and the like, of 4-(6,11-dihydrodibenzo-[b.e.]-thiepin-11-one-3-yl)-4-oxobutyric acid are converted to 4-(6,11-dihydrodibenzo-[b.e.]-thiepin-11-one-3-yl)-4-oxobutyric acid.

In like manner, substituting the salts, e.g., potassium, sodium, ammonium, calcium, amine, and the like, of 4-(8-methoxy-6,11-dihydrodibenzo-[b.e.]-thiepin-11-one-3-yl)-4-oxobutyric acid and
4-(8-chloro-6,11-dihydrodibenzo-[b.e.]-thiepin-11-one-3-yl)-4-oxobutyric acid is productive of
4-(8-methoxy-6,11-dihydrodibenzo-[b.e.]-thiepin-11-one-3-yl)-4-oxobutyric acid and
4-(8-chloro-6,11-dihydrodibenzo-[b.e.]-thiepin-11-one-3-yl)-4-oxobutyric acid, respectively.

EXAMPLE 14

One g. of methyl 4-(6,11-dihydrodibenzo-[b.e.]-thiepin-11-one-3-yl)-4-oxobutyrate is dissolved in 500 ml. of toluene containing 5 g. of n-octanol and 0.5 g. of p-toluenesulfonic acid. The reaction mixture is heated in a nitrogen atmosphere and a total of 350 ml. of toluene is slowly distilled out over a period of 5 hours. The reaction mixture is cooled and concentrated to about 10 ml. by evaporation under reduced pressure. The residue is then chromatographed on 200 g. of silica gel eluting with hexane:ethyl acetate (1:8) to yield octyl 4-(6,11-dihydrodibenzo-[b.e.]-thiepin-11-one-3-yl)-4-oxobutyrate.

Similarly, other lower esters (e.g., the propyl ester) of 4-(6,11-dihydrodibenzo-[b.e.]-thiepin-11-one-3-yl)-4-oxobutyric acid can be transesterified to a higher ester (e.g., the decyl ester) of 4-(6,11-dihydrodibenzo-[b.e.]-thiepin-11-one-3-yl)-4-oxo-butyric acid.

In like manner lower esters (e.g., the methyl ester) of 4-(8-methoxy-6,11-dihydrodibenzo-[b.e.]-thiepin-11-one-3-yl)-4-oxobutyric acid and 4-(8-chloro-6,11-dihydrodibenzo-[b.e.]-thiepin-11-one-3-yl)-4-oxobutyric acid are converted to the higher esters (e.g., the octanyl ester) of 4-(8-methoxy-6,11-dihydrodibenzo[b.e.2-thiepin-11-one-3-yl)-4-oxobutyric acid and 4-(8-chloro-6,11-dihydrodibenzo-[b.e.]-thiepin-11-one-3-yl)-4-oxobutyric acid, respectively.

EXAMPLE 15

Five hundred mg. of dodecyl 4-1 6,11-dihydrodibenzo-[b.e.]-thiepin-11-one-3-yl)-4-oxobutyrate is refluxed with 250 ml. of absolute ethanol containing 10 mg. of sodium cyanide for 18 hours in a nitrogen atmosphere. The reaction mixture is cooled and evaporated under reduced pressure to yield a residue which is chromatographed on 100 g. of silica gel eluting with hexane:ethyl acetate (1:8) to yield ethyl 4-(6,11-dihydrodibenzo-[b.e.]-thiepin-11-one-3-yl)-4-oxobutyrate.

Similarly, other higher esters (e.g., the nonyl ester) of 4-(6,11-dihydrodibenzo-[b.e.]-thiepin-11-one-3-yl)-4-oxobutyric acid can be transesterified to a lower ester (e.g., the hexyl ester) of 4-(6,11-dihydrodibenzo-[b.e.]-thiepin-11-one-3-yl)-4-oxobutyric acid.

In like manner, higher esters (e.g., the dodecyl ester of 4-(8-methoxy- and 8-chloro-6,11-dihydrodibenzo-[b.e.]-thiepin-11-one-3-yl)-4-oxobutyric acid are converted to the lower esters (e.g., the ethyl ester) of 4-(8-methoxy- and 8-chloro-6,11-dihydrodibenzo-[b.e.]-thiepin-11-one-3-yl)-4-oxobutyric acid.

EXAMPLE 16

| Ingredients | Quantity per tablet, mgs. |
|---|---|
| 4-(6,11-dihydrodibenzo-[b.e.]-thiepin-11-one-3-yl)-4-oxo-butyric acid | 150 |
| cornstarch | 40 |
| sucrose | 200 |

The above ingredients are thoroughly mixed and pressed into single scored tablets.

EXAMPLE 17

| Ingredients | Quantity per tablet, mgs. |
|---|---|
| 4-(6,11-dihydrodibenzo-[b.e.]-thiepin-11-one-3-yl)-4-oxobutyric acid | 25 |
| cornstarch | 100 |
| lactose | 393 |
| magnesium stearate | 2 |

The above ingredients are mixed intimately and pressed into single scored tablets.

15 Mg. of 4-(8-methoxy- or 8-chloro-6,11-dihydrodibenzo-[b.e.]-thiepin-11-one-3-yl)-4-oxobutyric acid is substituted for the 25 mg of the unsubstituted compound of the above composition.

EXAMPLE 18

| Ingredients | Quantity per capsule, mgs. |
|---|---|
| potassium 4-(6,11-dihydrodibenzo-[b.e.]-thiepin-11-one-3-yl)-4-oxybutyrate | 150 |
| lactose | 190 |

The above ingredients are mixed and introduced into a hard-shell gelatin capsule.

EXAMPLE 19

| Ingredients | Quantity per capsule, mgs. |
|---|---|
| calcium 4-(6,11-dihydrodibenzo-[b.e.]-thiepin-11-one-3-yl)-4-oxobutyrate | 150 |
| lactose | 182 |
| magnesium stearate | 8 |

The above ingredients are mixed and introduced into a hard-shell gelatin capsule.

EXAMPLE 20

| Ingredients | Quantity per tablet, mgs. |
|---|---|
| isopropylammonium 4-(6,11-dihydrodibenzo-[b.e.]-thiepin-11-one-3-yl)-4-oxobutyrate | 150 |
| cornstarch | 100 |
| lactose | 370 |
| magnesium stearate | 2 |

The above ingredients are mixed intimately and pressed into single scored tablets.

EXAMPLE 21

| Ingredients | Quantity per capsule, mgs. |
|---|---|
| methyl 6,11-dihydrodibenzo-[b.e.]-thiepin-11-one-3-yl)-4-oxo-butyrate | 25 |
| lactose | 225 |

The above ingredients are mixed and introduced into a No. 1 hard-shell gelatin capsule.

EXAMPLE 22

| Ingredients | Quantity per tablet, mgs. |
|---|---|
| 4-(6,11-dihydrodibenzo-[b.e.]-thiepin-11-one-3-yl)-4-oxobutyric acid | 150 |
| sucrose | 245 |

The above ingredients are thoroughly mixed and processed into single scored tablets, one tablet being administered every three to four hours.

EXAMPLE 23

| Ingredients | Quantity per tablet, mgs. |
|---|---|
| isoamyl 4-(6,11-dihydrodibenzo-[b.e.]-thiepin-11-one-3-yl)-4-oxobutyrate | 200 |

| Ingredients | Quantity per tablet, mgs. |
|---|---|
| cornstarch | 100 |
| lactose | 368 |
| magnesium stearate | 2 |

The above ingredients are mixed intimately and pressed into single scored tablets.

EXAMPLE 24

| Ingredients | Quantity per capsule, mgs. |
|---|---|
| 4-(6,11-dihydrodibenzo-[b.e.]-thiepin-11-one-3-yl)-4-oxobutyric acid | 25 |
| lactose | 225 |
| dextrose | 10 |

The above ingredients are mixed and introduced into a hard-shell gelatin capsule.

12.5 Mg. of 4-(8-methoxy- or 8-chloro-6,11-dihydrodibenzo-[b.e.]-thiepin-11-one-3-yl)-4-oxobutyric acid is substituted for the 25 mg of the unsubstituted compound of the above composition.

EXAMPLE 25

| Ingredients | Quantity per capsule, mgs. |
|---|---|
| methyl 4-(6,11-dihydrodibenzo-[b.e.]-thiepin-11-one-3-yl)-4-oxobutyrate | 150 |
| lactose | 99 |

The above ingredients are mixed and introduced into a hard-shell gelatin capsule.

EXAMPLE 26

| Ingredients | Quantity per tablet, mgs. |
|---|---|
| isoamyl 4-(6,11-dihydrodibenzo-[b.e.]-thiepin-11-one-3-yl)-4-oxobutyrate | 200 |
| lactose | 135 |
| magnesium stearate | 5 |

The above ingredients are mixed and pressed into single tablets.

EXAMPLE 27

| Ingredients | Quantity per tablet, mgs. |
|---|---|
| calcium 4-(6,11-dihydrodibenzo-[b.e.]-thiepin-11-one-3-yl)-4-oxobutyrate | 150 |
| cornstarch (paste | 50 |
| magnesium stearate | 0.8 |
| lactose | to 500 |

The above ingredients are thoroughly mixed and pressed into single scored tablets.

EXAMPLE 28

| Ingredients | Quantity per tablet, mgs. |
|---|---|
| potassium 4-(6,11-dihydrodibenzo-[b.e.]-thiepin-11-one-3-yl)-4-oxobutyrate | 125 |
| cornstarch | 38 |
| magnesium stearate | 0.76 |
| polyvinylpyrrolidone | 17 |
| lactose | to 380 |

The above ingredients are mixed intimately and pressed into single scored tablets.

EXAMPLE 29

| Ingredients | Quantity per capsule, mgs. |
|---|---|
| isopropylammonium 4-(6,11-dihydrodibenzo-[b.e.]-thiepin-11-one-3-yl)-4-oxobutyrate | 250 |
| cornstarch | 38 |
| lactose | to 380 |

The above ingredients are mixed and introduced into a hard-shell gelatin capsule.

EXAMPLE 30

| Ingredients | Quantity per capsule, mgs. |
|---|---|
| isoamyl 4-(6,11-dihydrodibenzo-[b.e.]-thiepin-11-one-3-yl)-4-oxobutyrate | 300 |
| lactose | 72 |
| magnesium stearate | 8 |

The above ingredients are mixed and introduced into a hard-shell gelatin capsule.

EXAMPLE 31

An injectable preparation buffered to a pH of 8.5 is prepared having the following composition:

| | | |
|---|---|---|
| 4-(6,11-dihydrodibenzo-[b.e.]-thiepin-11-one-3-yl)-4-oxo-butyric acid | 0.2 | g |
| $K_2HPO_4$ buffer (0.4 M solution | 2 | ml. |
| KOH (1N) | 8.6 | ml. |
| water (sterile) | to 20 | ml. |

0.15 G. of 4-(8-methoxy- or 8-chloro-6,11-dihydrodibenzo-[b.e.]-thiepin-11-one-3-yl)-4-oxobutyric acid is substituted for the 0.2 g. of the unsubstituted compound of the above composition.

EXAMPLE 32

A suppository totaling 2.8 grams is prepared having the following composition:

| | |
|---|---|
| 4-(6,11-dihydrodibenzo-[b.e.]-thiepin-11-one-3-yl)-4-oxo-butyric acid | 25 mg. |
| Witepsol H-15 (triglycerides of saturated vegetable fatty acids; a product of Riches-Nelson, Inc., New York, N.Y.) | balance |

20 Mg. of 4-(8-methoxy- or 8-chloro-6,11-dihydrodibenzo-[b.e.]-thiepin-11-one-3-yl)-4-oxobutyric acid is substituted for the 25 mg of the unsubstituted compound of the above composition.

EXAMPLE 33

An oral suspension for pediatric use is prepared having the following composition:

| | | |
|---|---|---|
| 4-(6,11-dihydrodibenzo-[b.e.]-thiepin-11-one-3-yl)-4-oxo-butyric acid | 0.25 | g. |
| fumaric acid | 0.5 | g. |
| sodium chloride | 2.0 | g. |
| methyl paraben | 0.1 | g. |
| granulated sugar | 25.5 | g. |
| sorbitol (70% solution) | 12.85 | g. |
| Veegum K (Vanderbilt Co.) | 1.0 | g. |
| flavoring | 0.035 | ml. |
| colorings | 0.5 | mg. |
| distilled water | to 100 | ml. |

0.15 G. of 4-(8-methoxy- or 8-chloro-6,11-dihydrodibenzo-[b.e.]-thiepin-11-one-3-yl)-4-oxobutyric acid is substituted for the 0.25 g. of the unsubstituted of the above composition.

EXAMPLES 34-35

Powdered top dressings for veterinary use are prepared having the following compositions:

| | Ex. 34 | Ex. 35 |
|---|---|---|
| 4-(6,11-dihydrodibenzo-[b.e.]-thiepin-11-one-3-yl)-4-oxo-butyric acid | 0.2 g. | 0.4 g |
| sucrose | 5.7 g. | 3.7 g. |
| polyvinyl pyrrolidone | 0.3 g. | 0.3 g. |

0.15 G. of 4-(8-methoxy- or 8-chloro-6,11-dihydrodibenzo-[b.e.]-thiepin-11-one-3-yl)-4-oxobutyric acid is substituted for the 0.2 g. of the unsubstituted compound of the composition of Example 34.

0.3 G. of 4-(8-methoxy- or 8-chloro-6,11-dihydrodibenzo-[b.e.]-thiepin-11-one-3-yl)-4-oxobutyric acid is substituted for the 0.4 g. of the unsubstituted compound of the composition of Example 35.

EXAMPLE 36

A suppository totaling 2.8 grams is prepared having the following composition:

| | |
|---|---|
| 4-(6,11-dihydrodibenzo-[b.e.]-thiepin-11-one-3-yl)-4-oxo-butyric acid | 275 mg. |
| Witepsol H-15 | balance |

EXAMPLE 37

BIODATA

Test for Anti-Inflammatory Activity Utilizing Carrageenin-Induced Paw Inflammation in the Rat.

Protocol: Simonsen female rats weighing 80-90 grams are used. The test materials are given at hour 0 orally by gavage in 1 ml. of aqueous vehicle. At hour 1, 0.05 ml of a 1% solution (in 0.9% NaCl) of carrageenin is injected into the right hind paw. This injection causes an inflammation of the paw. The rats are sacrificed at hour 4, at which time both hind paws are removed and weighed separately.

End point: % increase in paw size calculated as follows:

$$\frac{\text{Wt. of Right Paw} - \text{Wt. of Left Paw}}{\text{Wt. of Left Paw}} \times 100$$

Using the above protocol it is determined that 4-(6,11-dihydrodibenzo-[b.e.]-thiepin-11-one-3-yl)-4-oxobutyric acid and 4-(8-methoxy-6,11-dihydrodibenzo-[b.e.]-thiepin-11-one-3-yl)-4-oxobutyric acid have 27 (95% confidence limits: 10-66) and 35 (95% confidence limits: 13-128) times, respectively, the anti-inflammatory activity of phenylbutazone.

What is claimed is:

1. A compound of the formula:

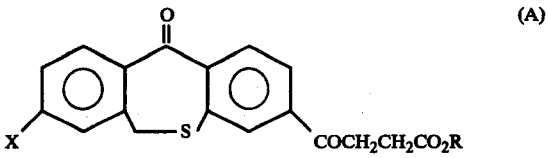

(A)

wherein X is hydrogen, methoxy or chloro, and R is hydrogen, an alkyl group containing from one to twelve carbon atoms, or a pharmaceutically acceptable salt thereof when R is hydrogen.

2. The compound of claim 1 wherein X and R are both hydrogen, 4-(6,11-dihydrodibenzo-[b.e.]-thiepin-11-one-3-yl)-4-oxobutyric acid.

3. The compound of claim 1 wherein X is methoxy and R is hydrogen, 4-(8-methoxy-6,11-dihydrodibenzo-[b.e.]-thiepin-11-one-3-yl)-4-oxobutyric acid.

4. The compound of claim 1 wherein X is chloro and R is hydrogen, 4-(8-chloro-6,11-dihydrodibenzo-[b.e.]-thiepin-11-one-yl)-4-oxobutyric acid.

5. The compound of claim 1 wherein X is hydrogen and R is methyl, methyl 4-(6,11-dihydrodibenzo-[b.e.]-thiepin-11-one-3-yl)-4-oxobutyrate.

6. The compound of claim 1 wherein X is methoxy and R is methyl, methyl 4-(8-methoxy-6,11-dihydrodibenzo-[b.e.]-thiepin-11-one-3-yl)4-oxobutyrate.

7. The compound of claim 1 wherein X is chloro and R is ethyl, ethyl 4-(8-chloro-6,11-dihydrodibenzo-[b.e.]-thiepin-11-one-3-yl)-4-oxobutyrate.

8. The sodium salt of the compound of claim 1 wherein X is hydrogen, sodium 4-(6,11-dihydrodibenzo-[b.e.]-thiepin-11-one-3-yl)-4-oxobutyrate.

9. The potassium salt of the compound of claim 1 wherein X is methoxy, potassium 4-(8-methoxy-6,11-dihydrodibenzo-[b.e.]-thiepin-11-one-3-yl)-4-oxobutyrate.

10. The calcium salt of the compound of claim 1 wherein X is chloro, calcium 4-(8-chloro-6,11-dihydrodibenzo-[b.e.]-thiepin-11-one-3-yl)-4-oxobutyrate.

11. The copper salt of the compound of claim 1 wherein X is hydrogen, copper 4-(6,11-dihydrodibenzo-[b.e.]-thiepin-11-one-yl)-4-oxobutyrate.

12. The isopropylammonium salt of the compound of claim 1 wherein X is hydrogen, isopropylammonium 4-(6,11-dihydrodibenzo-[b.e.]-thiepin-11-one-3-yl-oxobutyrate.

13. A composition for treating inflammation, pain or pyrexia in mammals consisting essentially of a pharmaceutically acceptable non-toxic excipient and a therapeutically effective amount of a compound represented by the formula:

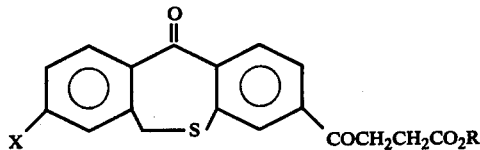

wherein X is hydrogen, methoxy or chloro, and R is hydrogen, an alkyl group containing from one to twelve carbon atoms, or a pharmaceutically acceptable salt thereof when R is hydrogen.

14. A method of treating inflammation, pain or pyrexia in mammals which comprises administering to a mammal suffering therefrom a therapeutically effective amount of a compound represented by the formula:

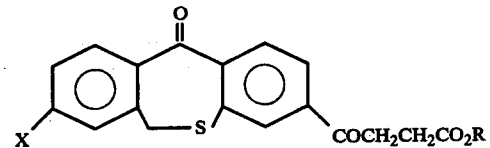

wherein X is hydrogen, methoxy or chloro, and R is hydrogen, an alkyl group containing from one to twelve carbon atoms, or a pharmaceutically acceptable salt thereof when R is hydrogen.

15. A composition for administration to a pregnant mammal to delay the onset of parturition consisting essentially of a pharmaceutically acceptable non-toxic excipient and a therapeutically effective amount of a compound represented by the formula:

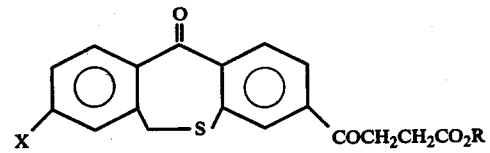

wherein X is hydrogen, methoxy or chloro, and R is hydrogen, an alkyl group containing from one to twelve carbon atoms, or a pharmaceutically acceptable salt thereof when R is hydrogen.

16. A method comprising administering to a pregnant mammal to delay the onset of parturition a compound selected from the group of compounds represented by the formula:

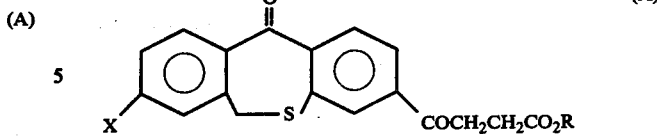

wherein X is hydrogen, methoxy or chloro, and R is hydrogen, an alkyl group containing from one to twelve carbon aoms, or a pharmaceutically acceptable salt thereof when R is hydrogen.

17. The method of claim 16 wherein said pregnant mammal has had a previous spontaneous abortion, miscarriage or premature delivery, which occurred prior to the time for normal parturition at or about full term.

18. The method of claim 17 wherein said pregnant mammal is a woman who is not suffering from inflammation, pyrexia or nonparturition-causing pain but who is experiencing uterine muscle contractions, said compound being administered in a therapeutically effective amount adapted to reduce the intensity or duration of the uterine muscle contractions, stop the uterine muscle contractions altogether, whereby termination of the pregnancy is postponed from the time it otherwise would have happened.

19. Process for the production of 4-(8X-6,11-dihydrodibenzo-[b.e.]-thiepin-11-one-yl)-butyric acid compounds having the formula:

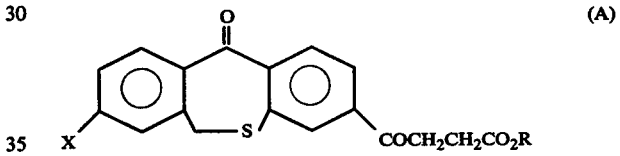

wherein X is hydrogen, methoxy or chloro, and R is hydrogen, an alkyl group containing from one to twelve carbon atoms, or a pharmaceutically acceptable salt thereof when R is hydrogen, which comprises one or more of the following steps:
 (a) converting an alkyl 2-carboalkoxy-4-(8X-6,11-dihydrodibenzo-[b.e.]-thiepin-11-one-3-yl)-4-oxobutyrate to its corresponding acids, the compounds of Formula (A) wherein R is hydrogen;
 (b) esterifying an acid of Formula (A) to obtain a corresponding $C_1$–$C_{12}$ alkyl ester thereof;
 (c) converting an acid of Formula (A) to a pharmaceutically acceptable salt thereof;
 (d) hydrolyzing an ester of Formula (A) to obtain the corresponding salt or free acid thereof;
 (e) transesterifying a lower ester of Formula (A) to obtain a higher ester thereof;
 (f) transesterifying a higher ester of Formula (A) to obtain a lower estert thereof;
 (g) converting a salt of Formula (A) to the corresponding free acid;
 (h) converting a salt of Formula (A) to another salt by a salt interchange.

* * * * *